(12) United States Patent
Monteleone et al.

(10) Patent No.: US 7,165,221 B2
(45) Date of Patent: Jan. 16, 2007

(54) SYSTEM AND METHOD FOR NAVIGATING PATIENT MEDICAL INFORMATION

(75) Inventors: Rand Monteleone, Acton, MA (US); John E. Auer, Ipswich, MA (US); Paul Gilman, Gloucester, MA (US)

(73) Assignee: Draeger Medical Systems, Inc., Danvers, MA (US)

( * ) Notice: Subject to any disclaimer, the term of this patent is extended or adjusted under 35 U.S.C. 154(b) by 553 days.

(21) Appl. No.: 10/008,125

(22) Filed: Nov. 5, 2001

(65) Prior Publication Data

US 2002/0065686 A1 May 30, 2002

Related U.S. Application Data

(60) Provisional application No. 60/248,086, filed on Nov. 13, 2000.

(51) Int. Cl.
*G06F 3/00* (2006.01)
(52) U.S. Cl. ...................... 715/738; 715/781
(58) Field of Classification Search ............. 715/738, 715/739, 781, 810, 804, 866; 705/2, 3; 600/300, 600/301; 128/920, 903, 904
See application file for complete search history.

(56) References Cited

U.S. PATENT DOCUMENTS

| 5,210,872 | A | 5/1993 | Ferguson et al. | 395/650 |
|---|---|---|---|---|
| 5,262,943 | A | 11/1993 | Thibado et al. | 364/413.01 |
| 5,560,005 | A | 9/1996 | Hoover et al. | 395/600 |
| 5,713,350 | A | 2/1998 | Yokota et al. | 128/630 |
| 5,715,823 | A | 2/1998 | Wood et al. | 128/660.01 |
| 5,772,585 | A | 6/1998 | Lavin et al. | 600/300 |
| 5,832,450 | A | 11/1998 | Myers et al. | 705/3 |
| 5,842,173 | A * | 11/1998 | Strum et al. | 705/1 |
| 5,842,175 | A | 11/1998 | Andros et al. | 705/3 |
| 5,903,889 | A | 5/1999 | de la Huerga et al. | |
| 5,910,799 | A | 6/1999 | Carpenter et al. | 345/333 |
| 5,920,870 | A | 7/1999 | Briscoe et al. | 707/103 |

(Continued)

FOREIGN PATENT DOCUMENTS

EP  0 668 047 A2  8/1995

(Continued)

OTHER PUBLICATIONS

Solar Lab Access System General Information, Apr. 1998.

(Continued)

*Primary Examiner*—Kieu D. Vu
(74) *Attorney, Agent, or Firm*—Jack Schwartz & Associates

(57) ABSTRACT

A network compatible user interface system and method are presented for supporting navigation through patient medical information. The system comprises a communication processor for acquiring a patient group identifier allocated to a grouping of patients and for acquiring medical information associated with the patients. A display generator operates to generate a composite display window incorporating a first window including the patient group identifier and a list of patients in the grouping and a second window for displaying different medical information corresponding to different medical applications. The different medical information is associated with patients within the patient grouping. A display navigation processor maintains the first window display while displaying different medical information in the second window in response to user navigation between the different applications.

15 Claims, 14 Drawing Sheets

U.S. PATENT DOCUMENTS

| | | | |
|---|---|---|---|
| 5,924,074 A | 7/1999 | Evans | |
| 5,926,175 A | 7/1999 | Sturgeon et al. | 345/327 |
| 5,995,937 A * | 11/1999 | DeBusk et al. | 705/2 |
| 6,018,713 A | 1/2000 | Coli et al. | |
| 6,038,566 A | 3/2000 | Tsai | 707/102 |
| 6,064,673 A | 5/2000 | Anderson et al. | 270/389 |
| 6,125,350 A | 9/2000 | Dirbas | 705/2 |
| 6,226,620 B1 * | 5/2001 | Oon | 705/2 |
| 6,734,880 B1 * | 5/2004 | Chang et al. | 715/738 |
| 2002/0178031 A1 * | 11/2002 | Sorensen et al. | 705/2 |
| 2003/0083903 A1 * | 5/2003 | Myers | 705/2 |

FOREIGN PATENT DOCUMENTS

| | | |
|---|---|---|
| WO | WO 98/13751 | 4/1998 |
| WO | WO 00/46781 | 8/2000 |

OTHER PUBLICATIONS

QS Workstation General Information, Apr. 1998.
HP M2000A Patient Documentation Center, Mar. 1998.
Metavision, Jun. 1998.
Tour Metavision, Jun. 1998.
Tour Workflow Support, Jun. 1998.
Solar Lab Access System Functionality Comparison, document not provided.
Carevue Cinical Information System Agilent Technologies, copy not provided.
Tour Data Entry, Jun. 1998.
Tour Analysis, Jun. 1998.
Healthcare Information Systems, Oct. 1998.
Agilent Technologies Viridia Documentation Center, Jan. 2001.
HP Carevue Data Reporting Solution, 1997.
McDonald, CJ et al., "The Regenstrief Medical Record System:a quarter century experience", Internat'l Journal of Medical Informatics, vol. 54, No. 3, Jun. 1999, pp. 225-253.
Sung, M.Y. et al., "CoMed: a real time collaborative medicine system", Internat'l Journal of Medical Informatics, vol. 57, No. 2-3, Jul. 2000, pp. 117-126.
Agilent Technologies, "CareVue Clinical Information System," Jan. 15, 2001, p. 1.
Marquette Medical Systems, "Solar Lab Access System General Information," Apr. 25, 1998, p. 1.
Hewlett Packard, "Physician Review System Functionality Comparison," 1997, pp. 2-6.
Hewlett Packard, "HP M2000A Central Data Management for the Critical Care Environment," Jun. 1996, p. 1336-1340.
Hewlett Packard, "HP CareVue Clinical Information System," May 1998, p. 1341-1346, Technical Information Guide.

* cited by examiner

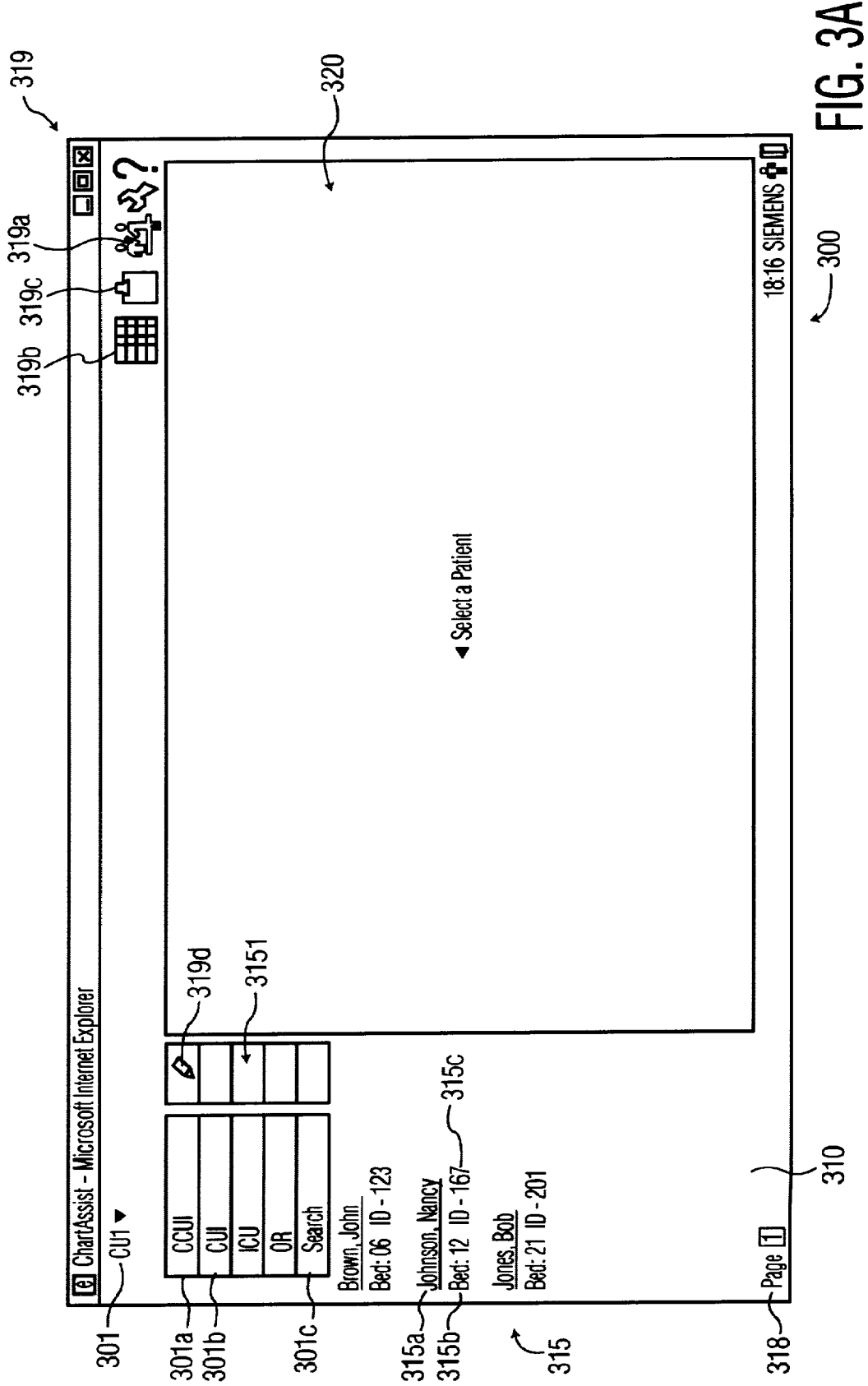

| Patient | Status | Vent | Diagnosis | Procedures | Labs | MD | RN |
|---|---|---|---|---|---|---|---|
| Madison, Paula ID: 321 bed: sting | | | PULMONARY VALVE DISORDER | Bypass surgery | △ | JDM | PEG |
| Templeton, Steve ID: 369 bed: cons | Liquid Diet | 16 hrs | LUNG LACERATION-OPEN | | △ | REF | DKL |
| Brown, John ID: 023-43-5436 bed: Bed 06 | | 2 hrs | TIBIA & FIBULA FRACTURE* | Pin Fibula | | | |
| Johnson, Nancy ID: 943-43-1645 bed: Bed 12 | Went to OR at 7:30 AM | | | | | | |
| Jones, Bob ID: 923-23-4356 bed: Bed 21 | | | TRAUMATIC BRAIN HEM NEC | | △ | | |

| Patient | Status | Vent | Diagnosis | Procedures | Labs | MD | RN |
|---|---|---|---|---|---|---|---|
| Brown, Robert ID: bed: Jup_02 | Family needs to speak with Dr. Smith when he gets in. | | CONGESTIVE HEART FAILURE | | | | |
| Simulated Patient Data ID: 321 bed: sting | | 7 hrs | LUNG LACERATION-OPEN | | A | | |
| Jones, Bob ID: 923-23-4356 | Went to OR at 7:30 AM | | TRAUMATIC BRAIN HEM NEC | | A | | |
| 3153 | | | | | | | |
| | | | | | | | |
| | | | | | | | |
| | | | | | | | |
| | | | | | | | |
| | | | | | | | |
| | | | | | | | |
| | | | | | | | |

11:10 SIEMENS

FIG. 8C

SYSTEM AND METHOD FOR NAVIGATING PATIENT MEDICAL INFORMATION

CROSS REFERENCE TO RELATED APPLICATIONS

This application claims the benefit of provisional U.S. application Ser. No. 60/248,086 filed Nov. 13, 2000.

FIELD OF THE INVENTION

This invention is related to the processing and displaying of medical information, and more particularly to processing and displaying of patient medical data associated with groupings of patients in a network environment.

BACKGROUND OF THE INVENTION

In hospitals and other health care environments, it is often necessary or desirable to collect and display a variety of medical data associated with a patient. Such information may include laboratory test results, care unit data, diagnosis and treatment procedures, ventilator information, attending physician or health care provider, and administrative or admission related information associated with a given patient.

Presently, such information is often provided via a chart attached to a patient's bedside or at an attendant's station. However, such physical charts are cumbersome to view, and often do not include the most up-to-date medical information associated with the patient. This problem is exacerbated due to the fact that such medical data arrives from multiple sources and at various times. Furthermore, present charts are not adapted to enable a physician or other care giver to easily access, view, or determine the results of multiple medical tests or other data associated with the patient. In addition, present techniques for navigating through a variety of patients' medical information are both tedious and inefficient, requiring extensive manual review and manipulation of physical chart information, or numerous selections via a user interface screen if information is available in electronic format. Moreover, tracking patients through multiple care units (e.g. from ER to CCU to ICU) presents a formidable problem using present techniques. Consequently, a need exists for a faster, more effective and user friendly means for navigating patient medical data associated with groupings of patients in a network environment including accessing, correlating, tracking and displaying patient medical information derived from a plurality of sources.

SUMMARY OF THE INVENTION

A network compatible user interface system and method are presented for supporting navigation through patient medical information. The system comprises a communication processor for acquiring a patient group identifier allocated to a grouping of patients and for acquiring medical information associated with the patients. A display generator operates to generate a composite display window incorporating a first window including the patient group identifier and a list of patients in the grouping and a second window for displaying different medical information corresponding to different medical applications. The different medical information is associated with patients within the patient grouping. A display navigation processor maintains the first window display while displaying different medical information in the second window in response to user navigation between the different applications.

In another aspect, the system of the present invention continuously acquires medical information associated with patients within the network. A patient relocation detector detects a relocation indicator contained in a message broadcast from a node on the network that indicates a patient has moved location in a care facility. This relocation indicator may be a flag set within the data base or on a name server uniquely identifying the patient with a new care facility and/or monitoring unit. A communication processor automatically acquires new information for the relocated patient in response to the relocation indication, wherein the new information comprises a patient group identifier allocated to a grouping of patients including the relocated patient, and medical monitoring information for the relocated patient at the new location.

In yet another aspect, the invention is embodied in a network compatible user interface system supporting navigation through patient medical information comprising a communication processor for acquiring patient medical information for storage in a data base and a menu generator for generating a menu prompting user selection of a field to be searched. A search engine searches the data base of acquired medical information to identify patients associated with search criteria determined by user selection of the field and entry of a text string. A display navigation processor automatically displays different medical information for the identified patients in response to user navigation between different applications.

The medical information displayed is based on patient data for those patients presently associated with a particular group ID such as an intensive care unit or emergency room unit. This is advantageous for automatically providing the most current, updated patient information associated with a given care unit. Such information includes patient identifier information, ventilator information, diagnosis information, procedure information, caregiver responsibility, and laboratory test result indicators.

BRIEF DESCRIPTION OF THE DRAWINGS

In the drawings:

FIGS. 3A–3C are exemplary illustrations of ways for navigating through a listing of patients and patient records according to an aspect of the present invention.

FIG. 5 shows an exemplary illustration of how patient information associated with a given care unit are displayed in board view mode according to an aspect of the present invention.

FIG. 6B provides an exemplary illustration of the resultant screen display associated with the flow diagram of FIG. 6A.

FIGS. 8A, 8B, 8C represent exemplary illustrations of search functions for retrieving and displaying patient information related to user-defined search criteria according to another aspect of the present invention.

DETAILED DESCRIPTION

Figure 1:
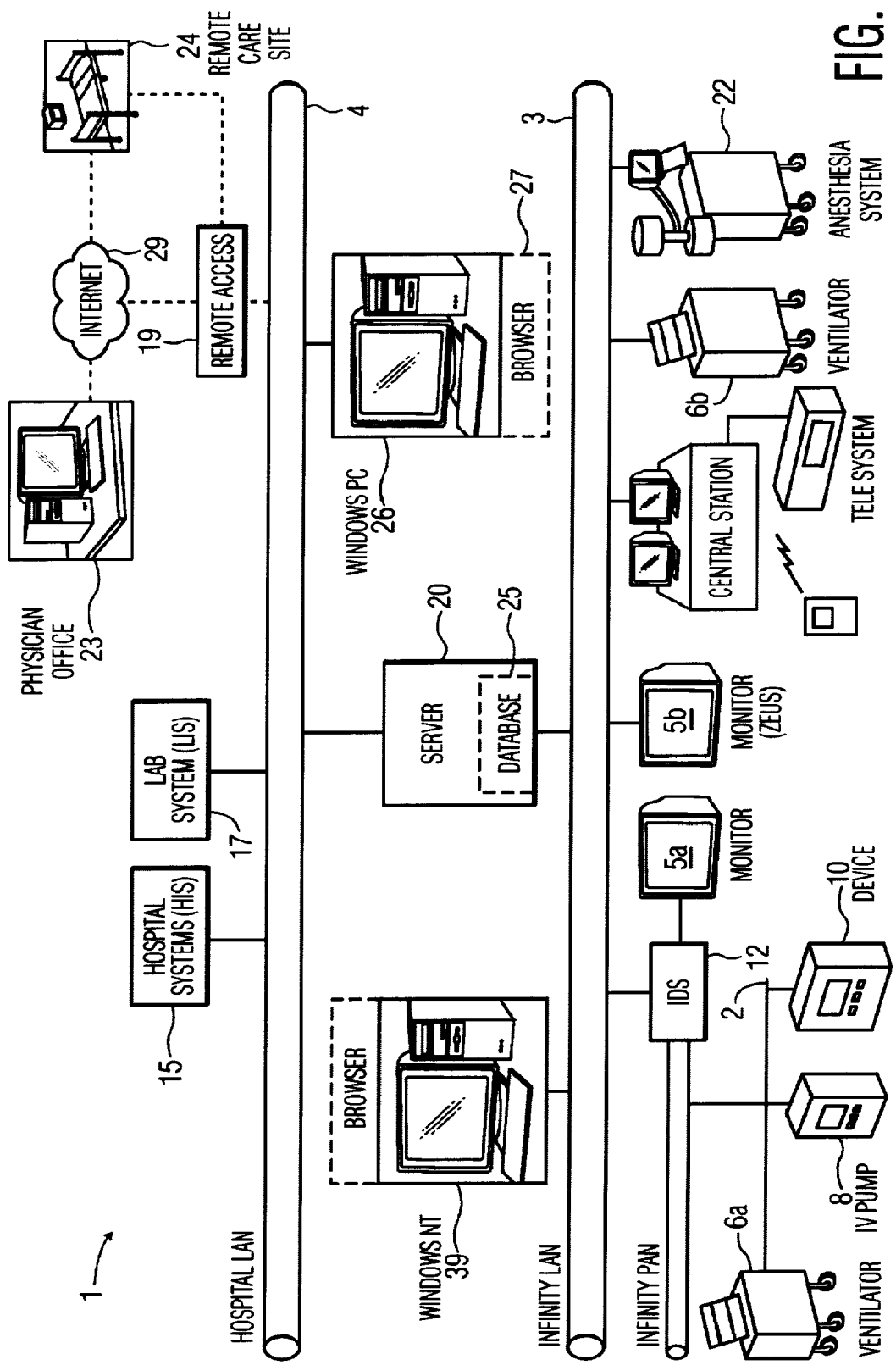
FIG. 1 is a block diagram of a communication network with various devices, according to the principles of the invention.

FIG. 1 is an exemplary block diagram of a communication network according to the principles of the present invention. Throughout the document, like reference numerals are used to indicate like parts. As shown in FIG. 1, communication network 1 is represented by an IP (Internet Protocol) compatible network with a hierarchy of local area and wide area networks interconnected together. It is to be noted that although the present exemplary hospital or medical network is an IP compatible network, other types of networks such as, but not limited to optical or wireless networks, using other computing protocols such as, but not limited to, for example, X.25, frame relay, IBM SNA etc., may also be used, as one skilled in the art can readily appreciate. In addition, although the exemplary network described is a hierarchical network, this is not required by the present invention. Any type of network architecture that provides communication connectivity among the devices on the network may be used.

As shown on FIG. 1, the first level of the exemplary hierarchical network 1 comprises a Medical Interface Bus (MIB) 2. A MIB is a well-known medical industry standard for locally connecting medical devices together. As shown in FIG. 1, MIB 2 is typically used to interconnect medical devices in a patient's room to administer care to a particular patient and to monitor the particular patient. Various medical devices may be connected via MIB 2; examples shown in FIG. 1 comprise a ventilator 6a, IV (Intravenous) Pump 8 or other medical equipment 10.

MIB 2 is typically connected to a second level LAN network 3 through an Interface Docking Station (IDS) device 12, for interfacing to Ethernet-compatible LAN network 3. The higher-level LAN 3 may be for example, an Infinity LAN, marketed by Siemens Medical System. This higher-level LAN 3 is typically, though not necessarily, used by a particular department within a hospital, such as an intensive care department or surgery department, etc., depending on the size of the organizations.

Although not shown in FIG. 1, more than one MIB may be connected to the second level LAN 3, so that more than one patient may be monitored or given care through LAN 3. In addition, medical devices may be connected directly to higher-level LAN 3. For example, as shown in FIG. 1, a ventilator 6b and an anesthesia system 13 are connected directly to LAN 3, without the need to go through a MIB.

Furthermore, LAN 3 may be interconnected to a Hospital LAN backbone 4 which also is Ethernet compatible. This backbone network 4 provides communication connectivity between various departments within a hospital or medical organization; for example, connecting hospital administrative systems 15 together with laboratory systems 17. In addition, the Hospital LAN 4 has a remote access gateway 19 which provides remote, secured access from, for example, a remote doctor's office 23 or a remote care site 24, to the various systems and devices on network 1, through for example, Internet 29. Alternatively, a remote site may also access the remote access gateway 19 directly through, for example, a dial-up telephone port, ADSL, or other types of private connection. Remote access gateway 19 may also be part of server 20, to be described below, instead of standing alone, as well know in the art.

According to the principles of the present invention, a central server 20 resides on LAN 3 for gathering and processing data from the peripheral medical devices or facilities coupled to LAN 3 or hospital LAN 4, including medical parameters such as lab results supplied via lab system 17 connected through an HL7 interface, for example. Additional medical parameter data including cardiology, hemodynamic, ventilation and neurology category data may also be acquired from any number of medical devices such as those shown in FIG. 1 and may be obtained at server 20 using various interface protocols including HL7 or ASTM messaging, for example. The acquired medical parameters associated with a given patient, including laboratory test results, are acquired from the medical devices on network 1 for display and control. One skilled in the art can readily recognize that server 20 may reside at any level of the hierarchy of network 1, since all the different levels of LANs (e.g., 3, or 4), as well as remote sites in FIG. 1 are interconnected together. An example of server 20, is a ChartAssist™ server, marketed by Siemens Medical System. The server may be hosted, for example, by a computer system that is capable of running Microsoft NT operating system.

Figure 2:
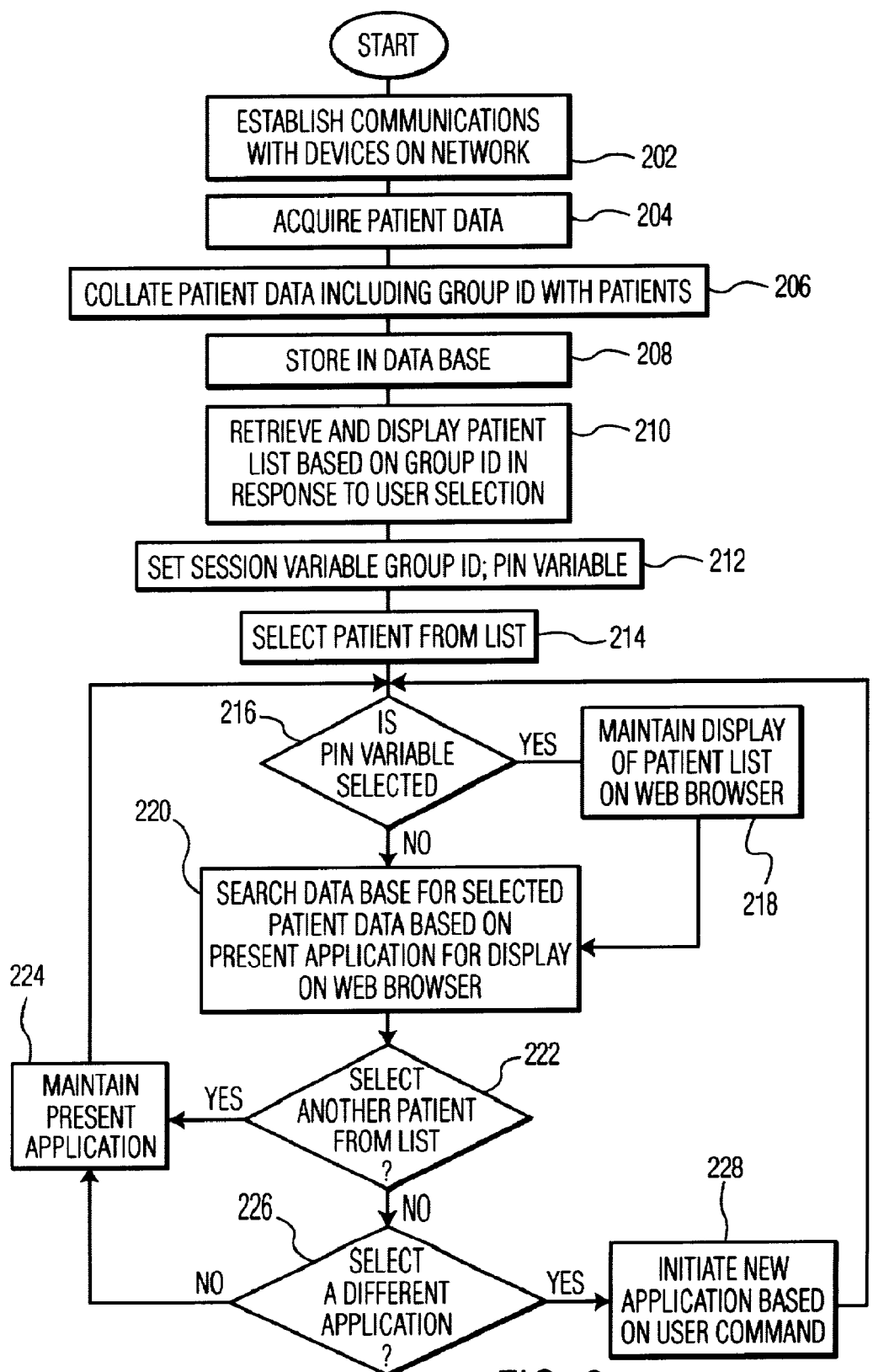
FIG. 2 represents a flow diagram of a process for searching and displaying patient information according to an aspect of the present invention.

FIG. 2 shows in flow chart form, functions that may be performed by server 20 in conjunction with the user interface software resident on a web browser 27 of a client computer 26 configured to navigate between applications in accordance with the present invention. Server 20 first establishes communications with devices on the network as shown in step 202. This is done, for example, by using IP protocol and the known IP device address for each device on the network 1, in conjunction with any higher application-layer protocols, as well known in the art.

Once communications are established between server 20 and the other devices, server 20 starts to acquire parameters that are being monitored and settings selected for the various devices. A communication processing module or software program operates to acquire the patient data including the monitored parameters and collate the information for storage in a data base. As previously mentioned, such parameter data may be obtained through an HL7 interface with LIS 17, or via ASTM or MIB point of care (POC) medical devices depicted in FIG. 1.

Medical parameter data including cardiology, lab results, hemodynamic, ventilation and neurology category data may be continuously or periodically acquired and correlated with a given patient for storage in relational data base 25 within server 20. Data base 25 may be of the type used for storing relational data such as the Microsoft SQL server. The acquired data may include time stamp information or other information indicative of the date and time associated with the acquired data.

Figure 9:
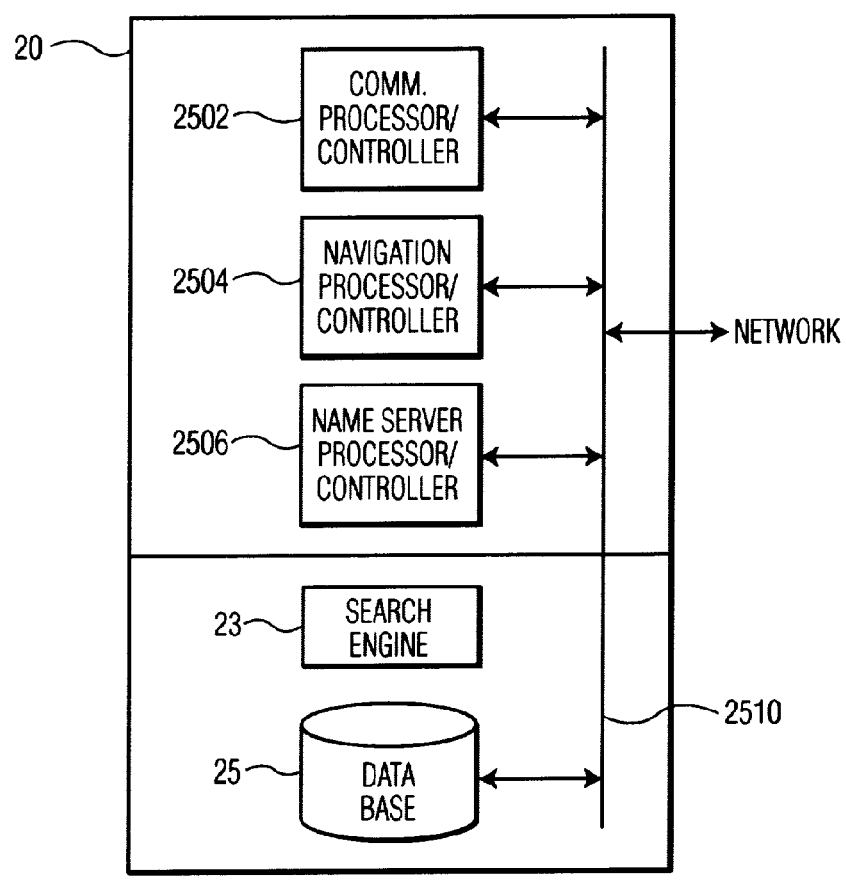
FIG. 9 is a block diagram of a server having functionality in accordance with the present invention.

Server 20 is therefore capable of collating and formatting medical data to be compatible with, for example, HTML (HyperText Mark-up Language) programming language for displaying data on a web browser having a graphical user interface (GUI) component. The server is also responsive to, for example, HTTP (HyperText Transfer Protocol) commands originated from a user's web browser for making a request. FIG. 9 shows a block diagram of an exemplary embodiment of the server 20 which operates to manage, collate, search and update the data base 25 (FIG. 1) containing patient medical information. Program elements or processors operative to carry out instructions for performing the various functions described herein include communications processing module 2502 (FIG. 9) that acquires the patient data including the monitored parameters and group identifiers allocated to patient groupings and collates the information for storage in data base 25. Navigation processor 2504 operates in conjunction with the web browser and display generator software to maintain display parameters for display to the user while navigating through various applications selected by a user through the user interface. Name server processor 2506 associates unique identifiers (Ids) with each node connected to the system network and with each patient in the system in order to track and update patient information throughout the system. Input/output data and control signals are used to communicate between the various processors as well as to interface with the data base 25 and search engine 23 and with the network via communication line 2510.

In one aspect of the present invention, a user may use a Microsoft Windows compatible PC 26 or Windows NT compatible PC 39 as shown in FIG. 1, or any other computers capable of running a menu generating program such as a web browser program (e.g., Microsoft Internet Explorer or Netscape Navigator, etc.) to view the aforementioned category type medical data associated with a given patient. That is, a user may use a web browser on any computer, as long as a communication connection can be made to server 20, to make request and view information acquired and stored in data base 25. This is advantageous, since a doctor may for example, gain access to medical parameter data from, for example, a remote physician's office 23, without having to access a dedicated terminal. Of course, a user can simply use a keyboard and/or a mouse or any other user interface devices to enter a user selection or request on a user computer, as is known in the art. The user interface contains functionality for maintaining a displayed listing of patients within a group while navigating between different applications operative to retrieve and display different medical data associated with a selected patient within the group. Such functionality includes a browser containing a display generator module for displaying a composite window containing both patient listing data and medical data associated with a selected patient. A navigation processor software module responsive to user input operates to maintain the displayed patient listing data while displaying different medical information in associated with the selected patient in response to user navigation between different applications.

Figure 3B:
Figure 3C:
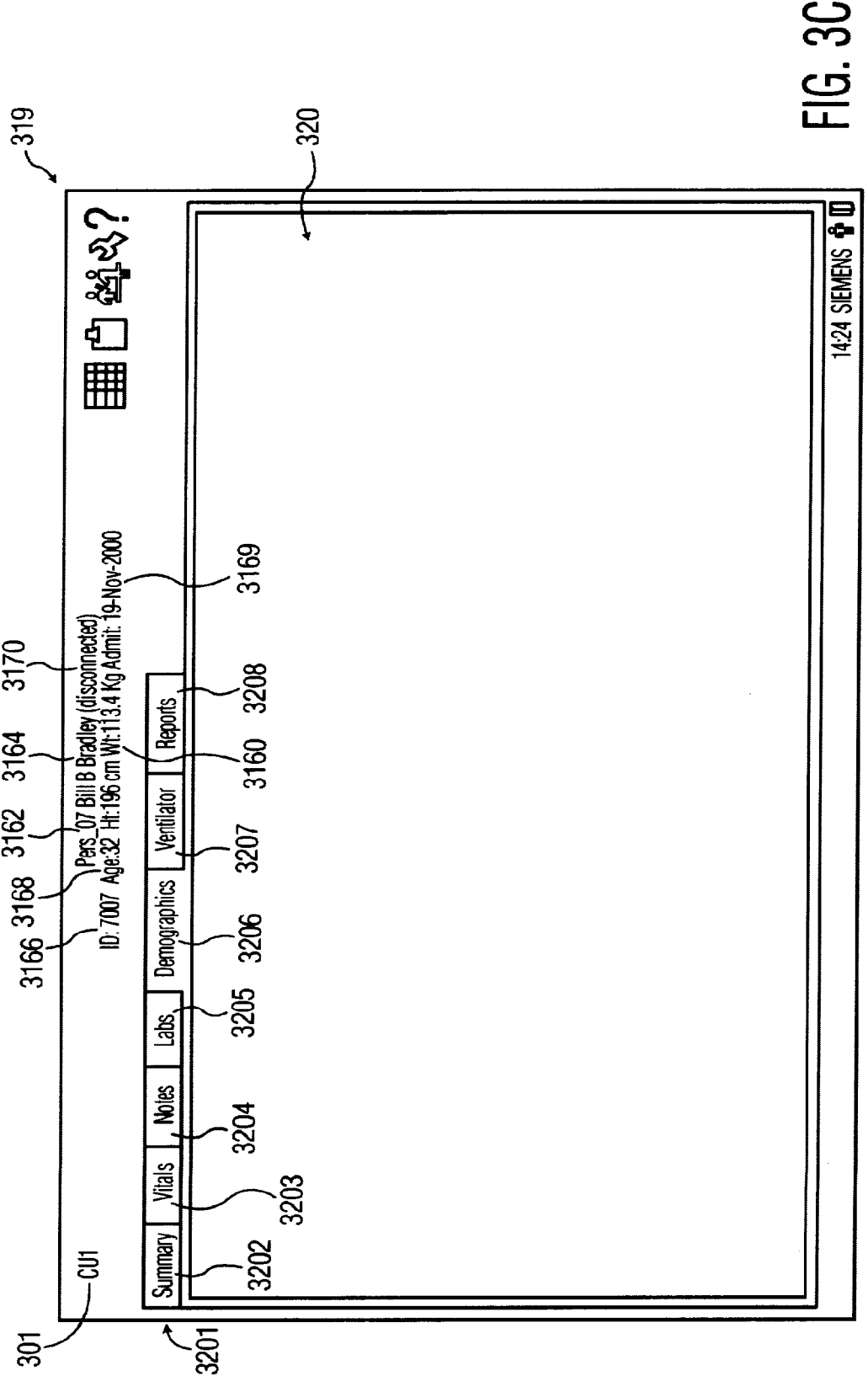

FIGS. 3A–3C are exemplary illustrations of a user interface system embodied in an aspect of the present invention for providing a flexible means of navigating through a listing of patients and/or patient records stored in the system data base 25. The listing of patients may be those patients currently admitted to the hospital or health care unit, or may be those patients identified within the network that are not yet admitted. In accordance with the present invention, the navigation mechanism may be based on particular care units or other user specified search criteria.

Referring now to FIG. 3A, there is shown an exemplary embodiment of a user interface display 300 that enables a user to view, select and acquire patient information associated with a given care unit. Composite display 300 comprises a first window portion 310 for viewing and manipulating patient and care unit information, and a second window portion 320 for displaying different medical information corresponding to different medical applications. Care unit label 301 comprises a display portion for displaying the current care unit and for providing a pull down list of all care units (e.g. 301A, 301B) monitored within the network for selection by the user. A search option 301c is also included within the selectable pull down menu via label 301 to provide a user-entered search of patient-related information. In an exemplary embodiment, a hospital may include a plurality of care units defined by category and organized within the relational data base to include one or more of an intensive care unit, critical care unit, maternity, gynecological or obstetrics care unit, emergency care unit, burn unit, neurological unit, surgical unit, pediatric or baby unit, infectious disease unit, and oncology unit. Note that a patient is typically assigned to a given care unit based on the particular medical needs of the patient relative to the type of care that each unit provides. In this manner, each patient may be allocated a group identifier (ID) associated with a particular care unit. It is of course, understood, that other group IDs may be used to associate certain patient data records within the data base 25 in relational fashion as is well known in the art.

Still referring to FIG. 3A, in conjunction with the flow chart depicted in FIG. 2, user selection (e.g. via mouse click) of the particular care unit causes a search of the data base 25 to display a listing 315 of the names of those patients associated with the selected care unit (or search string). The listing includes the patient name 315a, patient ID 315b, and bed label 315c, if applicable, for each patient. Formatting software operates to adapt the listing to the display screen. In the event the listing exceeds the space allocated for a given screen, a page selector 318 located at the lower left hand corner of window 310 enables a user to quickly access particular pages of displayed patient information viewable on display 300. In a preferred embodiment, the patient list is displayed in alphabetical order by last name. However, it is understood that the list may be displayed in a variety of different sort orders, such as by bed number or patient ID, for example.

User selection of the search option 301C from the selected care unit generates a pop-up entry panel 800 (see FIG. 8A) to be displayed to the user, prompting the user to enter a search string. Entry of the user-selected search string causes the search engine 23 within database 25 to search and retrieve a listing of patients within the database having a searchable record within the data base 25 that matches the user-entered search string.

Figure 4:
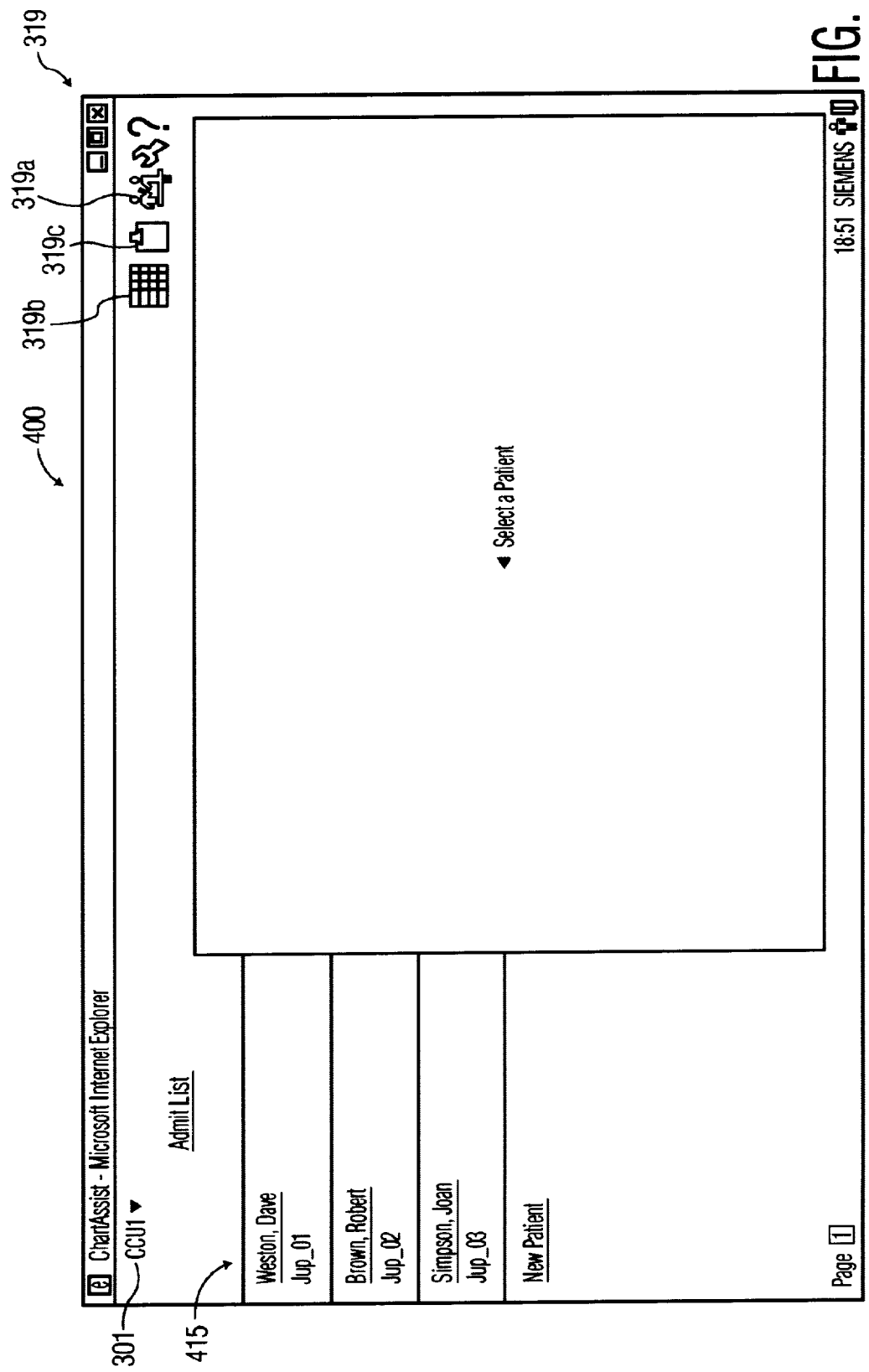
FIG. 4 is an exemplary illustration of how admission results data are displayed according to an aspect present invention.

A set of icons labeled generally as 319 positioned, for example, at the upper right hand corner of display 300 operates to provide quick access to basic functions associated with the system of the present invention. For example, user selection of admit icon 319a causes the user interface to generate display screen 400 shown in FIG. 4 which displays a list of all patients in the selected care unit (e.g. CCU) who are recognized within the network but who are not yet admitted to the system. That is, upon user selection of the admit mode of operation, a query is executed on server 20 and the user interface panel displays a list 415 of all patients in the selected care unit (CCU) having database entries defining their entry or connection within the communication network, but who are not yet admitted into the system. Subsequent selection of a given patient from the list of patients provides a link to an input screen for entering or updating relevant patient information including address data, physiological data, and admission date, as well as an input screen for entering physician and family contact information.

The system of the present invention operates to maintain identification of the selected care unit 301 throughout each of the system modes selectable via the set of icons 319, namely admit mode 319a, board view mode 319b, and patient view mode 319c. The system is operative in board view mode to provide a display containing certain medical information in a chart like format for each of the patients within the selected care unit. Patient view mode provides a display containing certain medical information associated a particular patient within the selected care unit.

For example, upon user selection of the board view icon 319b, the user interface processor displays a list of all patients in the selected care unit 301 that are currently admitted to the system. An exemplary illustration of such a screen is shown in FIG. 5 which identifies the care unit 301 and associated listing 315 of the patients, including patient name, patient ID, and bed number. Additional medical data is further included within the application window, including status 530, ventilator 540, diagnosis 550, procedure 560, lab results 570 and attendant area (MD/RN) 580. As previously mentioned, when the patient list exceeds the viewable page allocation, a page indicator 318 displays the number of pages in addition to the current page and provides a hyper link to the other pages.

Status field 530 provides a free text field into which a user or operator can enter textual information. This may be accomplished by data entry through a keyboard, light pen or other manual input means. Ventilator field 540 displays the current mode of ventilation associated with a given patient as well as the number of hours that the patient has been continuously ventilated. The ventilator field values and parameter settings may be automatically acquired from ventilator units connected via the network or may be entered by a user. Diagnosis field 550 operates to display the most recent primary and secondary diagnoses associated with each patient within the selected care unit, while procedure field 560 displays the most recent stored medical procedures for each patient.

Note that, upon user selection of a given patient from the listing of patients (see FIG. 3A or FIG. 5), patient specific information is accessed and retrieved from the data base 25 and displayed to the user in first window portion 310. By way of example, selection of a given patient labeled at 3151 from the census panel display 300 shown in FIG. 3A generates the display screen shown in FIG. 3C wherein a first window portion displays patient summary information 3160 at the top of the screen. As shown in FIG. 3C, the system of the present invention operates in a default mode to remove the list 315 of patients within the selected care unit upon selection of a particular patient from the list to enable a user to tab through various applications 3201 to view the particular patient's data. The summary information includes bed label 3162, patient name 3164, patient ID 3166, age, height and weight information 3168 and admission information 3169 such as the patient's admit date. Summary information display 3160 may further include an indicator 3170 if the patient is currently admitted to the system but is not currently active on the network. That is, if in response to a search request, the monitor or peripheral device to which a given patient had been connected to (via an associated node within the communication network) and who has been previously registered within the network is no longer responding, an indicator 3170 is displayed alerting the user to such detection. This may occur, for example, if a patient is removed from a ventilator unit, or may occur during transit from a given care unit (e.g. during transfer of a patient from an intensive care unit (ICU) to the operating room (OR)).

Navigation control processing is enabled by tabs labeled generally as 3201 which provide access to various applications for display in second window area 320. In the exemplary embodiment shown in FIG. 3C, such application tabs may comprise Summary 3202, Vitals 3203, Notes 3204, Labs3205, Demographics3206, Ventilator 3207 and Report 3208 tabs for launching corresponding applications for retrieving information from the data base 25 in accordance with predetermined search criteria. Each of the tabs 3201 may further include additional tab functions associated therewith to provide access to and processing of certain applications for display in window portion 320.

As previously discussed with respect to FIG. 3C, the system of the present invention in a default mode operates to remove the FIG. 3A list 315 of patients within the selected care unit upon selection of a particular patient from the list to enable a user to tab through various applications to view the particular patient's data. An advantageous feature of the present invention comprises selection icon 319d which operates, responsive to user selection of the icon, to maintain or "pin" the panel list 315 of patients within first window portion 310 even after a particular patient is selected. Pin icon 319d provides an indication to the user as to whether the list has been pinned (i.e. will be maintained for continued display). In an exemplary embodiment, such indication may be a visual indicator such as a different shape, font, or color attribute associated with pin indicator 319d. As shown in FIG. 3A, Pin indicator 319d is angled with respect to the vertical axis indicative of the default or "unpinned" mode of operation such that selection of a given patient from panel list 315 results in removal of the panel list in subsequent displays (see FIG. 3C). Mode activation/deactivation can be toggled by subsequent selections of Pin icon 319d.

FIG. 3B provides an exemplary illustration of the pinning functionality of the present invention for maintaining the first window display 310 containing the list of patients associated with the selected care unit while enabling display of different medical information in the second window 320 in response to user navigation between different applications. Referring now to FIG. 3B in conjunction with FIG. 3A, a user first selects pin icon 319d to enable the pin functionality for maintaining list 315. A particular patient 3151 is then selected from the list of patients within the selected care unit 301. The user further selects application tabs such as Notes tab 3204 and Diagnosis sub-tab 32041 to launch the Notes->diagnosis application for retrieving from the data base diagnostic information associated with the selected patient 3151 according to predetermined search criteria and displaying the results in window portion 320. At the same time, window portion 310 maintains the user-selectable list 315 of patients within the selected group or care unit 301. The resultant display is shown in FIG. 3B. Subsequent selection of a different patient 3153 within the given care unit causes that newly selected patient's data to be retrieved and loaded within the currently selected application tab. This advantageously enables "electronic rounds" within an application with minimal user interaction.

Figure 6A:
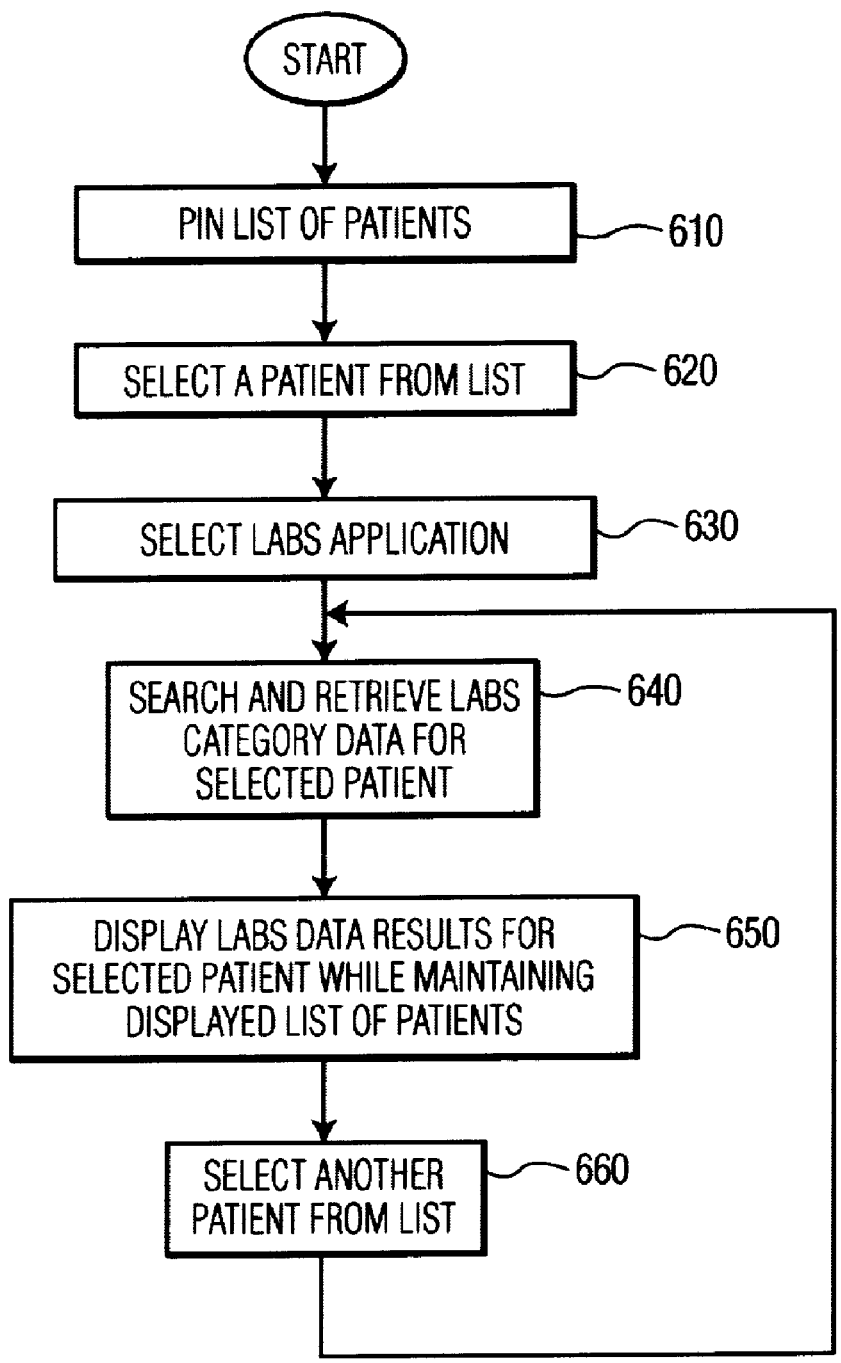
FIG. 6A represents a flow diagram for displaying application specific data while maintaining a list of grouped patients according to an aspect of the present invention.
Figure 6B:
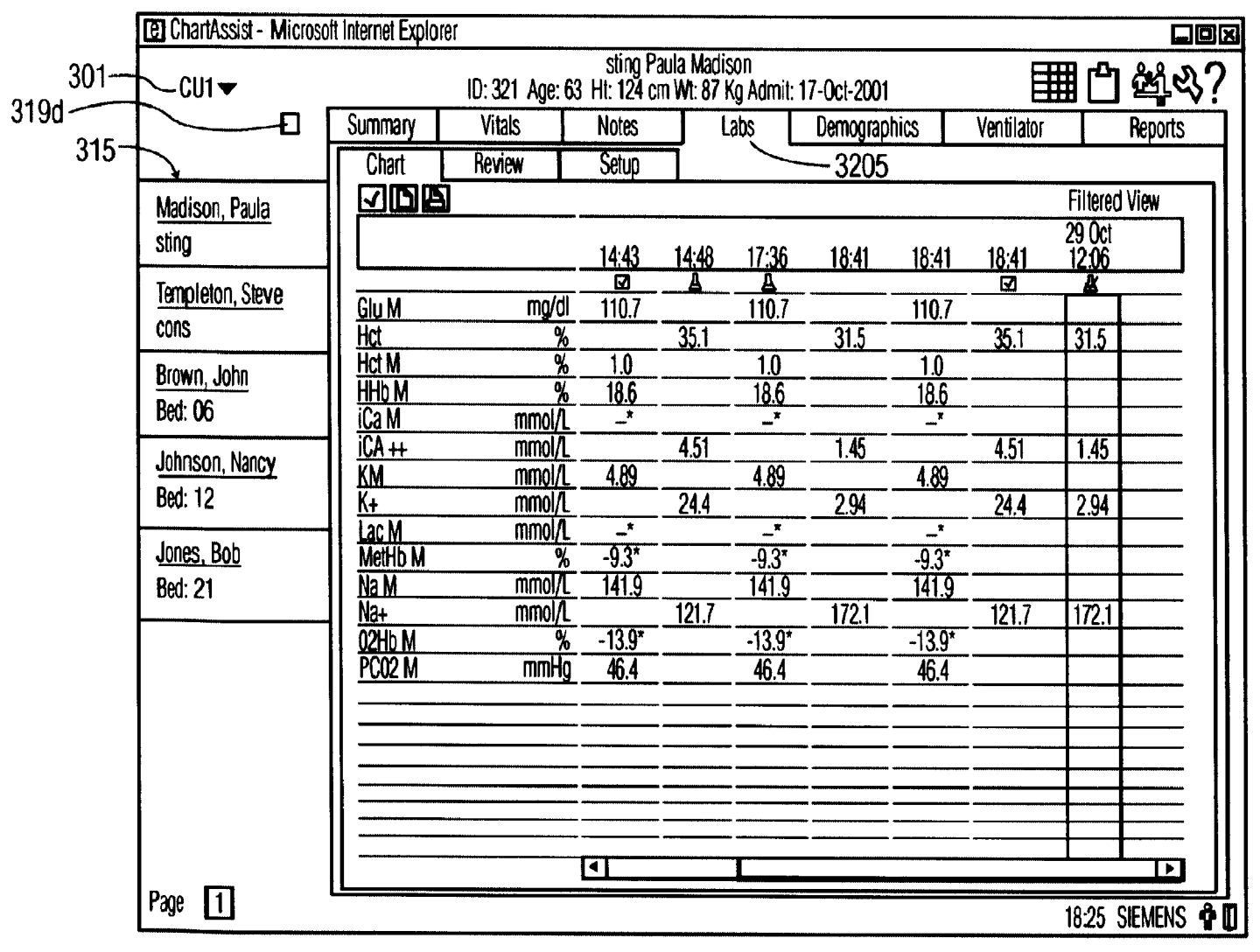

As a further example, FIG. 6A provides a flow chart illustration for displaying laboratory test results data for each patient within a given care unit. This is accomplished by pinning the panel listing 315 (step 610), selecting a given patient 3153 (step 620), selecting labs tab 3205 to view the labs result for that patient (steps 630, 640, 650) and then selecting each of the patients or selected patients within the list 315 (step 660). FIG. 6B provides an exemplary illustration of the resultant screen display associated with the aforementioned process. Note that a user may also navigate between different applications while maintaining the patient listing. For example, from the Notes->Diagnostic application displayed in FIG. 3B, user selection of the "Review" subtab 32042 causes execution of a data base query for retrieving information associated with this application. Display window 320 then displays the different medical data associated with the selected patient corresponding to the search and display criteria for the "Review" application. In similar fashion, selecting each of the tabs for demographics, ventilator, trends, summary and reports (see FIG. 3B) displays additional patient specific medical information corresponding to each of those categories of data based on specified search criteria for display to the user in window portion 320, while maintaining display of the list 315 of patients within that group in window portion 310.

The system of the present invention also operates to store in memory the last selected care unit that was viewed for each login account. In an exemplary embodiment, a data item record corresponding to the last selected care unit is stored in the data base and associated with that particular user account (e.g. user login). This record is then checked upon logging into the system, so that the user associated with that login will be placed in the care unit last selected in the previous session.

In another aspect, the system of the present invention enables a user to track a patient from one care unit to another within the hospital or health care environment. For example, a patient admitted into a hospital may move between different care units during his stay (e.g. from emergency room (ER) to intensive care unit (ICU)). Through the various nodes on the network LAN (e.g. hospital intranet) each associated with a given care unit and bed number, network connectivity with each of the medical devices (i.e. monitors) associated with a patient enables automatic tracking of the patient within the network. In an exemplary embodiment, server side software includes a network name server having a unique ID associated with each node and monitor device operative to communicate information to the server to automatically associate a particular node with a given patient connected to a given monitor on the network LAN. A memory card or smart card insertable into a monitor device connected to the network LAN at a given node may be used to identify and transfer associated medical information for that patient to another node within the network.

Figure 7:
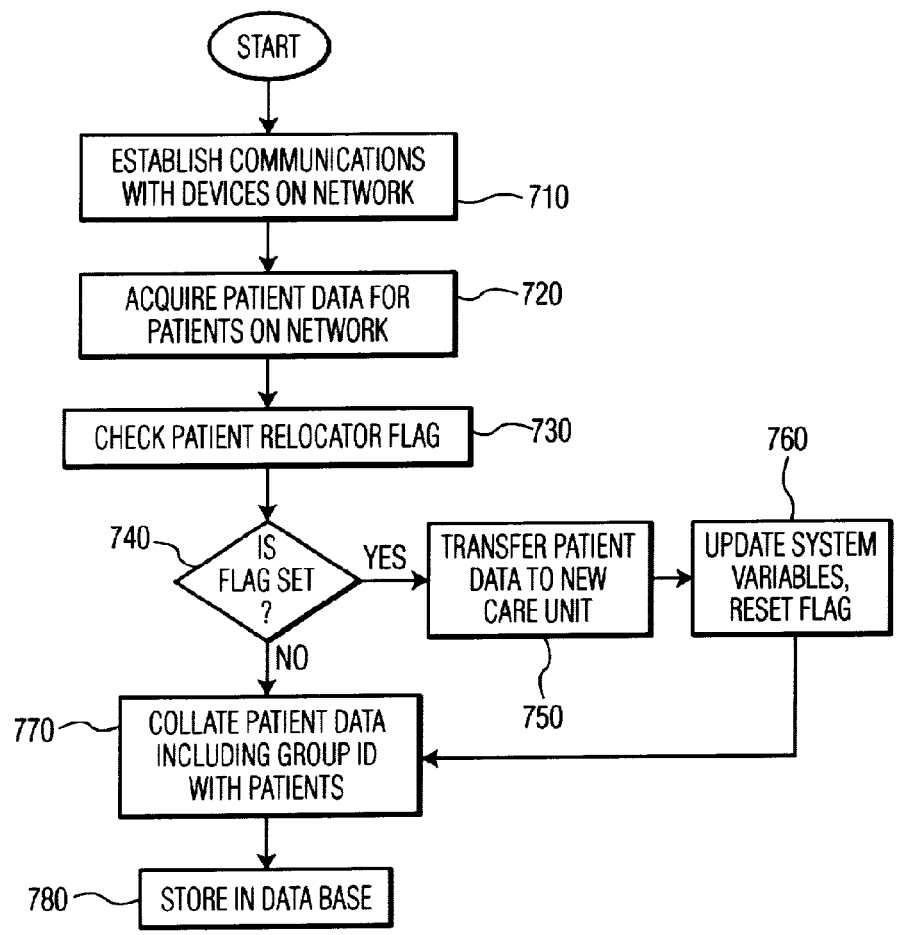
FIG. 7 represents a flow diagram for detecting, tracking and updating the location of a patient within the system according to another aspect of the present invention.

FIG. 7 provides an exemplary illustration of the process for detecting, tracking and updating the location of a patient within the system. This is accomplished by first establishing communications with each of the devices on the network (step 710). Once communications are established, patient data are acquired and processed by server side communications software program (step 720). A check of each patients' records is made to determine whether a relocation flag or indicator associated with a particular patient is set (step 730). If no flag is set, the system operates to collate the patient data including the group ID associated with each patient and store in the data base (steps 770–780). If, however, the check reveals a set relocation flag, a server processor module submits a request to the sending node requesting information including the patient's unique ID that is now associated with the new node. The system operates to determine the new group ID associated with the patient at the new location (i.e. node), and updates the information within the system, including the setting of new variables and parameters associating the patient with the new group ID. Medical parameter data stored within the system for that patient associated with the previous group ID is then transferred to associate with the new identifier (steps 750–780).

In this manner patient information may be obtained and updated to associate the patient with a new care unit. For example, a server side software communications processor receives periodic (e.g. every 20 seconds) informational updates (e.g. via broadcast messages) from each of the nodes on the system. The informational update messages comprise certain status information associated with the location of a particular patient associated with a node. When a patient moves from a given care unit and bed to a new care unit (and bed), tracking and association of the patient with the new care unit and node occurs in the following manner. First, an internal association of the monitor unit at that node connected with the patient takes place so that the node ID is associated with the patient now located at that node. A software process resident at the node then broadcasts a message containing this information over the LAN where it is received by the server 20 and analyzed. The information includes header information such as IP_address, the unique ID associated with that node, and additional data including patient name, monitor equipment status (e.g. on-line, off-line, standby), and a relocation indicator comprising a transfer flag which may be a bit or series of bits set in a predetermined manner such that the receiving software processor will recognize as a patient transfer. This prompts the server side software to interrogate the particular node by sending a network message requesting the identifier associated with that transferred patient. Upon receiving a response from the node, the server software will then look in its database 25 of unique patient ID's to locate the prior position of the patient. Server software then updates it's records based on the new node and sets internal parameters and session variables in order to collect monitoring data associated with that patient at that new node.

Figure 8A:
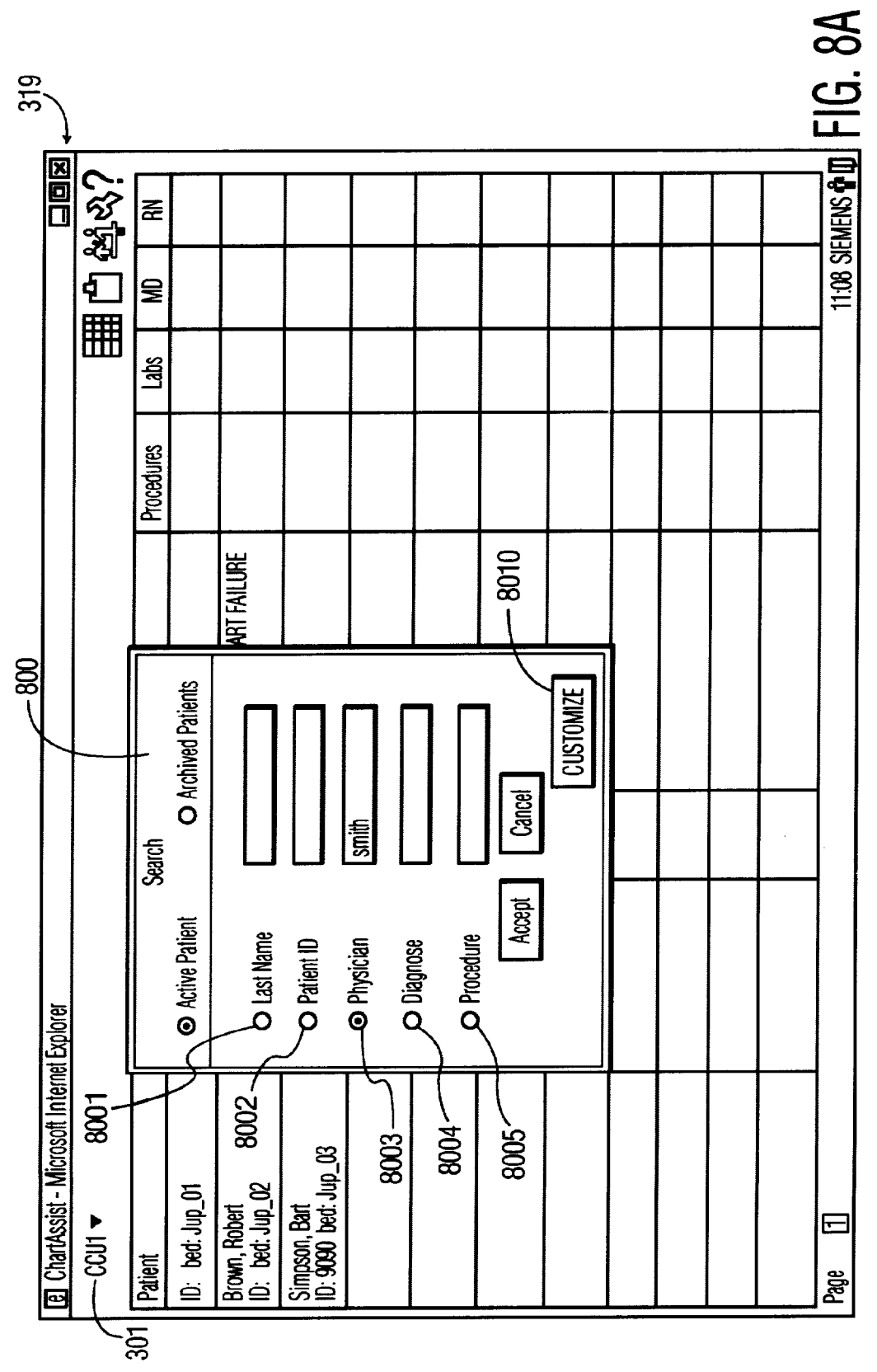

As previously mentioned with regard to FIG. 3A, user selection of search option 301c from the care unit list 301 generates a menu displaying a list of fields from which a user can search the data base to obtain medical information. An exemplary illustration is depicted in FIG. 8A. As shown therein, user selection of the search option 301C generates a pop-up menu panel 800 displayed to the user prompting the user to enter a search string. Entry of the user-selected search string causes the search engine within database 25 to search and retrieve a listing of patients within the relational database having a certain field or fields containing text that matches the search string for display to the user.

Figure 8C:
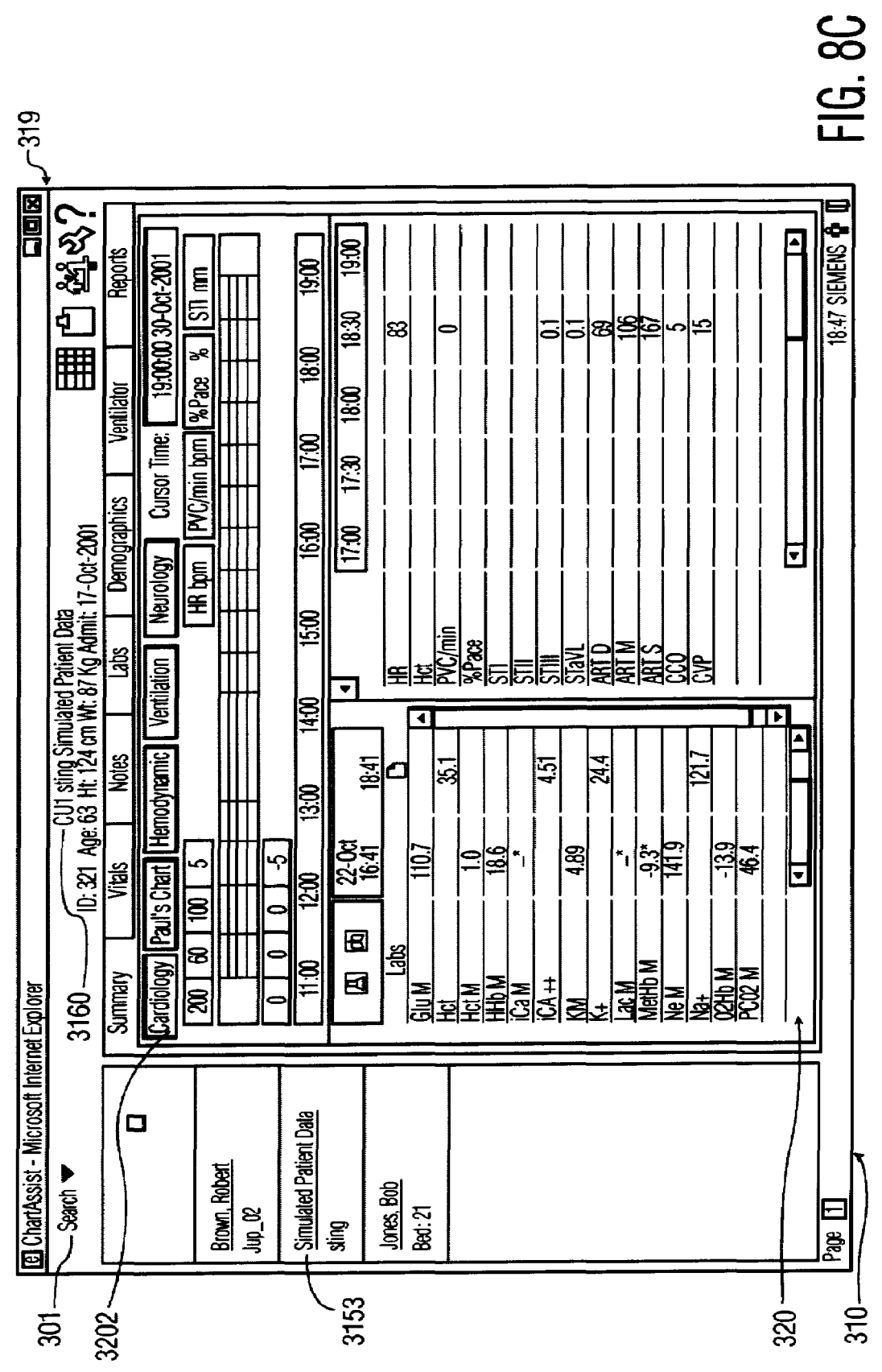

For example, the list of fields from which a user can search may include Last Name 8001, Patient ID 8002, Physician 8003, Diagnosis 8004, and Procedure 8005. Each of these fields is associated with particular medical information within the relational data base 25 such that when a user selects one of the fields and enters a search string, the user interface displays in window portion 310 a list 315 of all patients that match the user-specified criteria. As is understood, this list may span multiple care units and may be pinned by selection of pin icon 319d to maintain this display while navigating through various applications via the application tabs. For example, selecting the "Physician" field 8003 and entering the text string "smith" causes generation of a data base query executed by the search engine resident on server 20 for patients whose primary physician's last name includes the term "smith". As shown in FIG. 8B, and in similar fashion to that depicted in FIG. 5, a listing 315 of patients is returned in display window 310 along with associated medical information in window 320, corresponding to the system operative in board view mode (icon 319b). The user may then select each patient and navigate through the particular medical information available by means of the application tabs or icons to view desired data for that patient as previously discussed. As an example, FIG. 8C shows the results displayed to the user when a given patient 3153 is selected from the list 315 shown in FIG. 8B. That is, selection of a given patient causes application window 320 to execute a search and display the results of the Summary application tab 3202. The user may further navigate through additional medical data associated with the patient by means of additional patient selection, application selection, or care unit selection to obtain desired medical data.

In a further aspect, the search field 301c may include a further user selection 8010 (FIG. 8A) to enable a user to generate a "customized" care unit based on a user-specified criteria. For example, as shown in FIG. 8A entry of the term "Smith" in the "Physician" field and selection of the "customize" function 8010 causes the user interface display generator to store the user-assisted query on the system server associated with the given name to be retrieved and executed upon subsequent selection of the care label field 301 "Customize" search. If selected, the search criteria is stored in a session variable such that, even after a user logs off, a subsequent login and selection of the "customize" feature from the care unit list causes the software to invoke the customized query. This would enable a doctor, for example to obtain a list of her patients every time she logs in to the system.

It is to be understood that the embodiments and variations shown and described herein are for illustrations only and that various modifications may be implemented by those skilled in the art without departing from the scope of the invention.

What is claimed is:

1. A network compatible user interface system supporting navigation through patient medical information, comprising:
   a communication processor for acquiring a patient group identifier allocated to a grouping of patients and for acquiring medical information associated with said patients;
   a display generator for generating a composite display window incorporating
      a first window including said patient group identifier and a list of patients in said grouping; and
      a second window for displaying different medical information corresponding to different medical applications, said different medical information being associated with patients in said grouping of patients, said second window displaying different tabs corresponding to said different medical applications; and
   a display navigation processor for maintaining said first window display while displaying different medical information in said second window in response to user selection of one of said tabs and navigation between said different applications.

2. The system of claim 1, wherein said patient group identifier corresponds to one of a plurality of care units including two or more of (a) an intensive care unit, (b) a critical care unit, (c) maternity, gynecological or obstetric care unit, (d) emergency care unit, (e) burn unit, (f) neurological unit, (g) surgical unit, (h) pediatric unit, (i) infectious disease unit, and (j) oncology unit.

3. The system of claim 1, wherein said different medical information corresponding to different medical applications comprising two or more of (a) a diagnosis information, (b) laboratory test results, (c) ventilation unit information, (d) trend information, (e) administrative or admission related information.

4. The system of claim 1, wherein said first window further displays one or more of bed label, patient name, age, height, weight and admission date.

5. The system of claim 1, wherein said patient group identifier in said first window is user-selectable.

6. The system of claim 1, wherein said display navigation processor is responsive to user selection of a deactivation element in said first window display for no longer maintaining said list of patients in said first window during user navigation between said different applications.

7. The system of claim 1, wherein said patient group identifier is maintained in memory after user logout of the system.

8. A network compatible user interface system supporting navigation through patient medical information comprising:
   a communication processor for acquiring patient medical information for storage in a database;
   a menu generator for generating a menu prompting user entry and selection of at least one field to be searched, each field identifying a group of patients, said group of patients being associated with a respective group identifier;
   a search engine for searching said database of acquired medical information to identify patients associated with the group identifier indicated by search criteria determined by user selection of said field and entry of a text string; and
   a display processor for displaying a first window including said identified patients and automatically displaying in a second window different medical information corresponding to different medical applications, said different medical information for said patients identified to be associated with the group identified by the selected field in response to user navigation between different applications said display processor displaying in the second window different tabs corresponding to said different medical applications, wherein user selection of one of said tabs and navigation is performed by selecting one of said tabs; and
   wherein said display processor automatically displays different medical information for said identified patients for different applications in said second window without user re-entry of information determining said identified patients in said first window.

9. The system of claim 8, wherein said different applications comprise two or more of (a) a diagnosis information, (b) laboratory test results, (c) ventilation unit information, (d) administrative or admission related information.

10. The system of claim 8, wherein said at least one field comprises one or more of patient name, patient identifier, physician, diagnosis and procedure fields.

11. The system of claim 8, wherein said prompting menu further includes a selectable customization field responsive to a user command for generating a query based on said user-entered text string for subsequent execution without user re-entry of said text string.

12. An internet compatible method for displaying patient medical information, comprising:
   acquiring medical information associated with patients;
   collating said medical information including allocating a patient group identifier to a grouping of patients;
   generating a composite display window incorporating a first window including said patient group identifier and a list of patients in said grouping, and a second window for displaying different medical information corresponding to different medical applications, said different medical information being associated with patients in said grouping of patients, said second window displaying different tabs corresponding to said different medical applications; and maintaining said first window display while displaying different medical information in said second window in response to user selection of one of said tabs and navigation between said different applications.

13. The method of claim 12, wherein the step of maintaining further comprises setting a variable corresponding to a user command for retaining said list of patients in said first window.

14. The method of claim 12, wherein said first window further displays one or more of bed label, patient name, age, height, weight and admission date.

15. The method of claim 12, wherein said step of generating a composite display window further comprises generating a search menu for entering a text string in response to a user command.

* * * * *